(12) United States Patent
Söderlund et al.

(10) Patent No.: US 7,026,117 B2
(45) Date of Patent: Apr. 11, 2006

(54) METHOD FOR DETERMINING SPECIFIC NUCLEOTIDE VARIATIONS

(75) Inventors: Hans E. Söderlund, Espoo (FI); Anne-Christine Syvanen, Helsinki (FI)

(73) Assignee: Orchid BioSciences, Inc., Princeton, NJ (US)

( * ) Notice: Subject to any disclaimer, the term of this patent is extended or adjusted under 35 U.S.C. 154(b) by 0 days.

(21) Appl. No.: 09/258,216

(22) Filed: Feb. 26, 1999

(65) Prior Publication Data
US 2003/0082531 A1     May 1, 2003

Related U.S. Application Data

(63) Continuation of application No. 08/162,376, filed on Dec. 2, 1993, now Pat. No. 6,013,431, which is a continuation of application No. 07/656,575, filed on Feb. 15, 1991, now abandoned, which is a continuation-in-part of application No. 07/482,005, filed on Feb. 16, 1990, now abandoned.

(51) Int. Cl.
C12Q 1/68      (2006.01)
C12P 19/34    (2006.01)
C07H 21/04   (2006.01)

(52) U.S. Cl. ................ 435/6; 435/91.2; 536/24.3; 536/24.33

(58) Field of Classification Search ............ 435/5, 435/6, 91.2, 91.1; 536/23.1, 24.3, 24.33
See application file for complete search history.

(56) References Cited

U.S. PATENT DOCUMENTS

| 4,307,189 A | 12/1981 | Kit ................................. 435/6 |
| 4,563,419 A | 1/1986 | Ranki et al. .................... 435/6 |
| 4,656,127 A | 4/1987 | Mundy ........................... 435/6 |
| 4,683,195 A | 7/1987 | Mullis et al. ................... 435/6 |

(Continued)

FOREIGN PATENT DOCUMENTS

EP     123513     4/1984

(Continued)

OTHER PUBLICATIONS

Antonarakis, "Diagnosis of Genetic Disorders at the DNA Level," *N. Engl. J. Med.*, 320: 153-63 (1989).

(Continued)

*Primary Examiner*—Jehanne Sitton
(74) *Attorney, Agent, or Firm*—Kalow & Springut LLP

(57) ABSTRACT

Detection of variable nucleotide(s) is based on primer extension and incorporation of detectable nucleoside triphosphates. By selecting the detection step primers from the region immediately adjacent to the variable nucleotide, this variation can be detected after incorporation of as few as one nucleoside triphosphate. Labelled nucleoside triphosphates matching the variable nucleotide are added and the incorporation of a label into the detection step primer is measured. The selection of the detection step primer is important to the method according to this invention and is dependent on the nucleotide sequence of interest. The detection step primers are preferably selected so as to span the region immediately toward the 3' end from the variable nucleotide to be detected. The detection step primers can also be complementary to a sequence beginning several nucleotides removed from the variable nucleotide. The only limitation concerning the position of the detection step primers is that the sequence between the 3' end of the detection step primer and the variable nucleotide to be detected must not contain a nucleotide residue of the same type as the one to be detected. The detection step primers can equally well be chosen to be complementary to either the coding or non-coding strands of the nucleotide sequence of interest.

16 Claims, 3 Drawing Sheets

Detection Step Primer:   5'- Y Y Y Y Y Y Y Y  Y

Immobilized Target Sequence:   3'- X X X X X X X X (X)$_n$ X$_1$ X' X X X X X X X X - attachment - moiety
                                                              X$_2$ Added Nucleotide Triphosphate:   dY$_n$ and ddY$_1$* or ddY$_2$*
(only if X$_n$ ≠ X$_1$ or X$_2$)

U.S. PATENT DOCUMENTS

| | | | | |
|---|---|---|---|---|
| 4,683,202 | A | 7/1987 | Mullis | 435/6 |
| 4,734,363 | A | 3/1988 | Dattagupta et al. | |
| 4,760,017 | A | 7/1988 | McCormick | |
| 4,800,159 | A | 1/1989 | Mullis et al. | 435/91.2 |
| 4,840,892 | A | 6/1989 | Adams et al. | 435/6 |
| 4,851,331 | A | 7/1989 | Vary et al. | 435/6 |
| 4,863,849 | A | 9/1989 | Melamede | 435/6 |
| 4,883,750 | A | 11/1989 | Whiteley et al. | 435/6 |
| 4,962,020 | A | 10/1990 | Tabor et al. | 435/6 |
| 4,968,602 | A | 11/1990 | Dattagupta | 435/6 |
| 5,200,314 | A | 4/1993 | Urdea | |
| 5,221,518 | A | 6/1993 | Mills | |
| 5,310,893 | A | 5/1994 | Erlich et al. | 435/6 |
| 5,476,769 | A | 12/1995 | Soderlund et al. | |
| 5,846,710 | A * | 12/1998 | Bajaj | 435/6 |
| 5,888,819 | A * | 3/1999 | Goelet et al. | 435/5 |
| 6,004,744 | A * | 12/1999 | Goelet et al. | 435/5 |
| 6,013,431 | A * | 1/2000 | Soderlund et al. | 435/5 |

FOREIGN PATENT DOCUMENTS

| | | |
|---|---|---|
| EP | 237362 | 9/1987 |
| EP | 0238332 | 9/1987 |
| EP | 0246864 | 11/1987 |
| EP | 0288737 | 11/1988 |
| EP | 0297379 | 1/1989 |
| EP | 332435 | 3/1989 |
| EP | 333465 | 3/1989 |
| EP | 0317074 | 5/1989 |
| EP | 329311 | 8/1989 |
| EP | 329822 | 8/1989 |
| EP | 357011 | 8/1989 |
| EP | 332435 | 9/1989 |
| EP | 0332435 | 9/1989 |
| EP | 0333465 | 9/1989 |
| EP | 336731 | 10/1989 |
| EP | 370694 | 11/1989 |
| EP | 371437 A3 | 11/1989 |
| EP | 0357011 | 3/1990 |
| EP | 0370694 | 5/1990 |
| EP | 0 374 665 A2 | 6/1990 |
| EP | 0371437 | 6/1990 |
| EP | 0412883 | 2/1991 |
| EP | 412883 | 3/1991 |
| FR | 2650840 | 9/1989 |
| GB | 2202328 | 9/1988 |
| WO | 8603782 | 7/1986 |
| WO | 0297379 | 1/1989 |
| WO | 8909282 | 10/1989 |
| WO | WO89/09835 | 10/1989 |
| WO | 8910414 | 11/1989 |
| WO | 9001069 | 2/1990 |
| WO | 0899282 | 3/1990 |
| WO | 9006042 | 6/1990 |
| WO | WO90/09455 | 8/1990 |
| WO | 9011372 | 10/1990 |
| WO | WO90/11372 | 10/1990 |
| WO | WO89/10414 | 11/1990 |
| WO | WO 91 02087 | 2/1991 |
| WO | WO 91 13075 | 9/1991 |
| WO | WO 92 16657 | 10/1992 |

OTHER PUBLICATIONS

Bos, et al., "Prevalence of *ras* Gene Mutations in Human Colorecta Cancers," *Nature* 327:293-297 (1987).

Farr, et al., "Analysis of RAS Gene Mutations in Acute Myeloid Leukemia by Polymerase Chain Reaction and Oligonucleotide Probes," *Proc. Natl. Acad. Sci. U.S.A.*, 85: 1629-33 (1988).

Rall, S.C. Jr., et al., "Type III hyperlipoproteinemia associated with apolipoprotein E phenotype E3/3. Structure and genetics of an apolipoprotein E3 variant," *J. Clinical Investigation*, 83: 1095-1101 (1989).

Kerem, et al., "Identification of the Cystic Fibrosis Gene: Enetic Analysis," *Science* 245:1073-1080 (1989).

Kleppe, et al., "Studies on Polynucleotides," *J. Mol. Biol.*, 56: 341-61.

Mahley, "Apolipoprotein E: Cholesterol Transport Protein with Expanding Role in Cell Biology," *Science*, 240: 622-630 (1988).

McLean, et al., "Human Apolipoprotein E mRNA . . . " *J. Biol. Chem.* 259: 6498-6504 (1984).

McMahon, et al., "Characterization of c-Ki-RAS Oncongene . . . " *Proc. Natl. Acad. Sci. USA*, 84: 4974-4978 (1987).

Morel, et al., "Aspartic Acid at Position 57 of the HLA-DQ B Chain Protects Against Type I Diabetes: A Family Study," *Proc. Natl. Acad. Sci. USA*, 85:8111-8115, (1988).

Mullis and Faloona, "Specific Synthesis of DNA in vitro vs. Polymerase Catalyzed" *Chem. Reaction Meth. In Enzymol.* 155:335 (1987).

Mullis, "Unusual Origin of the Polymerase Chain Reaction," *Sci. Am.*, Apr. 1990: 56-65.

Scharf, et al., "HLA Class II Allelic Variation and Susceptibility to Pemphigus Vulgaris," *Proc. Natl. Acad. Sci. USA*, 85: 3504-3508 (1988).

Syvanen, et al., "A primer-guided nucleotide incorporation assay in the genotyping of apolipoprotein E," *Genomics* 8: 684-692 (1990).

Thomson, "HLA Disease Associations: Models for Insulin Dependent Diabetes Mellitus on the Study of Complex Human Genetic Disorders," *Annu. Rev. Genet.* 22: 31-50 (1988).

Syvanen et al., "Direct Sequence of Affinity-Captured Amplified Human DNA Application to the Detection of Apolipoprotein E Polymorphism", FEBS Letters, 258:71-74 (1989).

Syvanen et al., "Quantification of Polymerase Chain Reaction Products by Affinity-Based Hyprid Collection," Nucleic Acids Research, 16:11327-11339 (1988).

Ballabio et al., "PCR Test for Cystic Fibrosis Deletion", Nature, 343:220 (1990).

Grimberg et al., "A Simple and Efficient Non-Organic Procedure for the Isolation of Genomic DNA From Blood", Nucleic Acids Resarch, 17:8390 (1989).

Signer et al., "DNA Fingerprinting: Improved DNA Extraction From Small Blood Samples", Nucleic Acids Research, 16:7738 (1988).

Signer et al., "Modified Gel Electorphoresis for Higher Resolution of DNA Fingerprints", Nucleic Acids Research, 16:7739 (1988).

Mitchell et al., "Affinity Generation of Single Stranded DNA Following the Polymerase Chain Reaction: Application to Dideoxy Sequencing", WH 214 Journal of Cellular Biochemistry Supp. 13E 18th Annual Meeting (1989).

Smith, "DNA Sequence Analysis by Primed Synthesis", Methods in Enzymology, 65:560-581 (1980).

Kuppuswamy et al., "A New Use of Polymerase Chain Reaction (PCR) in Carrier Detection of Hemophilia-B Due to Point Mutations", Blood, The Journal of the American Society of Hematology, Thirty-First Annual Meeting of the American Society of Hematology, 74:957 (1989).

Rommens et al., "Identification of the Cystic Fibrosis Gene: Chromosome Walking and Jumping", Science, 245:1059-1065 (1989).

Riordan et al., "Identification of the Cystic Fibrosis Gene: Cloning and Characterization of Complementary DNA", Science, 245:1066-1072 (1989).

Wu et al., "Allele-specific Enzymatic Amplification of β-Globin Genomic DNA for Diagnosis of Sickle Cell Anemia", Proc. Natl. Acad. Sci. USA, 86:2757-2760 (1989).

Newton et al., "Analysis of Any Point Mutation in DNA. The Amplification Refractory Mutation System (ARMS)", Nucleic Acids Research, 17:2503-2516 (1989).

Ehlen et al., "Detection of Ras Point Mutations by Polymerase Chain Reaction Using Mutation-Specific Inosine-Containing Oligonucleotide Primers", Biochemical and Biophysical Research Communications, 160: 441-447 (1989).

Nassal et al., "PCR-Based Site-Directed Mutagenesis Using Primers With Mismatched 3'-Ends", Nucleic Acids Research, 18:3077-3078 (1990).

Caskey et al., "Disease Diagnosis by Recombinant DNA Methods", Science, 236:1223-1228 (1987).

Landegren et al., "DNA Diagnostics—Molecular Techniques and Automation", Science, 242:229-237 (1988).

Rossiter et al., "Molecular Scanning Methods of Mutation Detection", The Journal of Biological Chemistry, 265: 12753-12756 (1990).

Spitzer et al., "Replacement of Isoleucine-397 by Threonine in the Clotting Proteinase Factor IXa (Los Angeles and Long Beach Variants) Affects Macromolecular Catalysis but not L-tosylarginine Methyl Ester Hydrolysis", Biochem. J. 265: 219-225 (1990).

Kuppuswamy et al., "Single Nucleotide Primer Extension to Detect Genetic Diseases: Experimental Application to Hemophilia B (factor IX) and Cystic Fibrosis Genes", Proc. Natl. Acad. Sci. USA, 88:1143-1147 (1991).

Prober et al., "A System for Rapid DNA Sequencing With Fluorescent Chain-Terminating Dideoxynucleotides", Science, 238:336-341 (1987).

Landegren et al., "A Ligase-Mediated Gene Detection Technique", Science, 241:1077-1080 (1988).

Mikita et al., "Functional Consequences of the Arabinosylcytosine Structural Lesion in DNA", Biochemistry, 27:4698-4705 (1988).

Mullis et al., "Specific Synthesis of DNA in Vitro Via a Polymerase-Catalyzed Chain Reaction", Methods in Enzymology, 155:335-351 (1987).

Spitzer et al., "Molecular Defect in Factor $IX_{Bm\ Lake\ Elsinore}$", The Journal of Biological Chemistry, 263:10545-10548 (1988).

Ware et al.,"Genetic Defect Responsible for the Dysfunctional Protein: Factor $IX_{Long\ Beach}$", Blood, 72:820-822 (1988).

Wu, R. and Kaiser, A.D., "Structure And Base Sequence In the Cohesive Ends of Bacterophage Lambda DNA," Journal of Molecular Biology, 1968, pp. 523-537, vol. 35.

Skinner, J.A. and Eperon, I.C., "Misincorporation of AMV Reverse Transcriptase . . . Nucleotides," Nucleic Acids Research, 1986, pp. 6945-6964, vol. 14, No. 17*.

Hyman, E.D., "A New Method of Sequencing DNA," Anal. Biochem, 1988, pp. 423-436, vol. 174.

Delius, H., et al., "Separation of Complementary Strands of Plasmid DNA Using . . . Microscopy," Nucleic Acids Research, 1985, pp. 5457-5469, vol. 13.

Running, et al., "A Procedure for Productive Coupling of Synthetic Oligonucleotides . . . Caputure," Biotechniques, 1990, pp. 276-277, vol. 8.

Sokolov, B.P., "Primer Extension Technique for the Detection of Single Nucleotide In Genomic DNA," Nucleic Acids Research, 1990, p. 3671, vol. 18.

Alberts, B., et al., Molecular Biology of The Cell, Garland Publishing, Inc., New York, 1989, pp. 88-95, Second Edition.

EMI, et al., Genotyping and Sequence Analysis of Apolipoprotein E Genomics pp. 373-379, vol. 3, 1988.

* cited by examiner

Detection Step Primer: 5'- Y Y Y Y Y Y Y Y

Immobilized Target Sequence: 3'- X X X X X X X X X$_1$ X' X X X X X X X X X - attachment moiety $X_2$ Added Nucleotide Triphosphate:
a) ddY$_1$* or ddY$_s$*
b) ddY$_1$* or ddY$_2^+$
c) dY$_1$* (and ddY')
d) dY$_1$* and dY$_2^+$ (if X$_1$, X$_2 \neq$ X')

Figure 1

Detection Step Primer: 5'- Y Y Y Y Y Y Y Y

Immobilized Target Sequence: 3'- X X X X X X X X X (X)$_n$ X$_1$ X' X X X X X X X X - attachment - moiety
$\phantom{3'- X X X X X X X X X (X)_n X_1 X'}$ X$_2$ Added Nucleotide Triphosphate: dY$_n$ and ddY$_1^*$ or ddY$_2^*$
(only if X$_n$ ≠ X$_1$ or X$_2$)

Figure 2

METHOD FOR DETERMINING SPECIFIC NUCLEOTIDE VARIATIONS

This application is a continuation of application Ser. No. 08/162,376 filed Dec. 2, 1993, now U.S. Pat. No. 6,013,431, which is a continuation of application Ser. No. 07/656,575 filed Feb. 15, 1991, abandoned, which is a continuation in part of application Ser. No. 07/482,005 filed Feb. 16, 1990, abandoned.

TECHNICAL FIELD

The present invention relates to a method and reagents for determining specific nucleotide variations in a defined polynucleotide region, and to the use of this method in identifying specific point mutations and genetic variations.

BACKGROUND OF THE INVENTION

The genetic information of living organisms is carried in the nucleotide sequence of their genome. In the process of gene expression the nucleotide sequence is translated to amino acid sequences, i.e. proteins. Minor changes in the nucleotide sequence, even a single base substitution, may result in an altered protein product. The altered quality or quantity of given proteins changes the phenotype (i.e. the observable characteristics) of the organism or the cell, which for instance may be observed as a development of a disease.

The knowledge of the exact molecular defects causing inherited diseases, as well as predisposition to genetic disorders and cancer is increasing rapidly. The knowledge of the relevance of somatic mutations in malignancies is, however, limited due to the lack of rapid and reliable assay procedures for screening large numbers of samples.

Inherited diseases caused by point mutations include sickle cell anemia and β-thalassemias, which are caused by mutations in the β-globin gene. Antonarakis, 1989, New England J. Med., 320:153–163. These mutations generally involve the replacement, insertion or deletion of one to four nucleotides from the sequence of the normal gene. A large number of mutations in the β-globin gene that can lead to β-thalassemia have been characterized. Antonarakis, supra.

Other known inherited diseases caused by point mutations include α-thalassemia, phenylketonuria, hemophilia, α1-anti trypsin deficiency (Antonarakis, supra) and cystic fibrosis. Kere et al., 1989, Science, 245:1073–1080. Sickle cell anemia is caused by homozygosity for one unique base pair substitution in the sixth codon of the β-globin gene. Antonarakis, supra.

Cystic fibrosis is the most common autosomal recessive genetic disorder. It affects about 1/2000 individuals of Caucasian populations and consequently the carrier frequency is about 5%. The recent cloning and genetic analysis of the cystic fibrosis transmembrane regulator (CFTR) gene has revealed one major mutation, denoted ΔF508, which is a deletion of three nucleotides leading to loss of the phenylalanine at amino acid residue 508. Kerem et al., 1989, Science, 245:1073–1080. The prevalence of this mutation is on the average 68% in North American and European patient populations, the range being 40–88% in reports containing more than 100 CF chromosomes. Because of the high frequency of cystic fibrosis, efficient methods for the screening of carriers and for prenatal diagnosis are needed in the risk of group countries.

An example of a polymorphism which correlates to predisposition to disease is the three-allelic polymorphism of the apolipoprotein E gene. This polymorphism is due to single base substitutions at two DNA loci on the Apo E gene. Mahley, 1988, Science, 240:622–630. The polymorphism may explain as much as 10% of the individual variations in serum cholesterol levels. More than 90% of patients with type III hyperlipoproteinemia are homozygous for one of the Apo E alleles.

The human major histocompatibilty complex is a polymorphic system of linked genes located within a conserved region of the genome. The class II genes within the HLA-D (human leukocyte antigen) region encode a series of highly polymorphic alleles. Thomson, 1988, Annu. Rev. Genet., 22:31–50; Morel et al., 1988, Proc. Natl. Acad. Sci. USA, 85:8111–8115; and Scharf et al., 1988, Proc. Natl. Acad. Sci. USA, 85:3504–3508. This polymorphism has been shown to be associated with susceptibility to autoimmune diseases, such as insulin-dependent diabetes and pemphigus vulgaris.

The human ras-gene family, which includes the homologous H-, K- and N-ras genes, is one of the potential targets for mutational changes that play a role in human tumorigenesis. Point mutations in either codon 12, 13 or 61 of the ras genes have been shown to convert these genes into transforming oncogenes. Farr et al., 1988, Proc. Natl. Acad. Sci. USA, 85:1629–1633; and Bos et al., 1987, Nature, 327:293–297.

Somatic point mutations in the N-ras gene have been detected in association with acute myeloid leukemias (AML) and other hemotological malignancies). The N-ras mutations in AML occur predominantly in codons 12, 13 and 61 of the gene. A method for sensitive detection of the N-ras mutations in small quantities of leukemic cells amongst a vast majority of normal cells would constitute a most valuable tool in the follow-up of therapy of AML and other N-ras associated malignancies.

The detection of the specific base changes in the first and second position of codons 12, 13 and 61 of the N-ras gene requires either hybridization with a large number of different oligonucleotide probes, or direct nucleotide sequence determination of the amplified DNA. One critical aspect of both approaches is the proportion of cells containing the mutation. Depending on the method of choice a mutation must be present in 5–20% of the analyzed cell population to be detectable.

Point mutations and genetic variations in micro-organisms might lead to altered pathogenicity of resistancy to the therapeutics. The human immunodeficiency virus (HIV-1) can develop mutants which are resistant to zidovudine (AZT). The resistant virus isolates contain several point mutations, but three mutations seem to be common to all resistant strains: Asp 67-Asn (GAC--AAC), Lys 70-Arg (AAT-GAT) and Thr 215-Phe (ACC-TTC) or Tyr (ACC-TAC). Larder and Kemp, 1989, Science, 246:1155–1158.

It would therefore be significant if changes in nucleotide sequences in the genome of living organisms could be determined accurately and with such efficiency and ease that large numbers of samples could be screened. This would afford opportunities for pre- or postnatal diagnosis of hereditary predispositions or diseases and for detection of somatic mutations in cancer. Such a method could also be used for the selection of cells and strains for industrial biotechnology and for plant and animal breeding. Presently available methods suffer from drawbacks limiting their routine use.

Polymorphisms or mutations in DNA sequences are most commonly detected by hybridization to allele-specific oligonucleotide (ASO) probes. The nucleotide sequence of the ASO probes is designed to form either a perfectly matched hybrid or to contain a mismatched base pair at the site of the variable nucleotide residues. The distinction between a matched and a mismatched hybrid is based on i) differences in the thermal stability of the hybrids in the conditions used during hybridization or washing (European Patent Publication EP-237362), ii) differences in the stability of the hybrids analyzed by denaturing gradient electrophoresis or iii) chemical cleavage at the site of the mismatch (European Patent Publication EP-329311).

Oligonucleotides with 3' ends complementary to the site of the variable nucleotides have been used as allele-specific primers (European Patent Publication EP-332435). The identification of the variable nucleotide is based on the fact that a mismatch at the 3' end inhibits the polymerization reaction. A similar approach is used in oligomer ligation assays, in which two adjacent oligonucleotides are ligated only if there is a perfect match at the termini of the oligonucleotides (European Patent Publication EP-336731).

Cleavage of the DNA sequence with restriction enzymes can be utilized for identification of the variation, provided that the variable nucleotide alters, e.g. creates or destroys, a specific restriction site. Nucleotide sequencing is the most informative method for the determination of variable nucleotides.

The methods referred to above are relatively complex procedures, suffering from drawbacks making them difficult to use in routine diagnostics. The use of allele specific oligonucleotide probes requires careful optimization of the reaction conditions separately for each application. Fractionation by gel electrophoresis is required in several of the methods above. Such methods are not easily automatized.

SUMMARY OF THE INVENTION

We have now developed an improved method, which allows the detection of nucleotide variations. This method provides several advantages over prior art methods. The method according to this invention comprises few and easily performed procedures. It is especially suited for routine determinations of point mutations and nucleotide variations, such as single mismatches, deletions, insertions and inversions. The method according to the present invention allows quantification of the proportion of mutated cells in a sample as well as identification of mutations present in as little as about 0.5% of the analyzed cell population. Furthermore the complete protocol of the method disclosed is easily automated, which is becoming increasingly important in routine diagnostics.

The method of detection of the variable nucleotide(s) is based on primer extension and incorporation of detectable nucleoside triphosphates in the detection step. By selecting the detection step primers from the region immediately adjacent to the variable nucleotide, this variation can be detected after incorporation of as few as one nucleoside triphosphate.

Labelled nucleoside triphosphates matching the variable nucleotide are added and the incorporation of a label into the detection step primer is measured.

The selection of the detection step primer is important to the method according to this invention and is dependent on the nucleotide sequence of interest. The detection step primers are preferably selected so as to span the region immediately toward the 3' end from the variable nucleotide to be detected. The detection step primers can also be complementary to a sequence beginning several nucleotides removed from the variable nucleotide. The only limitation concerning the position of the detection step primers is that the sequence between the 3' end of the detection step primer and the variable nucleotide to be detected must not contain a nucleotide residue of the same type as the one to be detected. The detection step primers can equally well be chosen to be complementary to either the coding or non-coding strands of the nucleotide sequence of interest.

The target nucleic acid is preferably enriched by amplification in vitro to allow detection of one single variable nucleotide in the human genome. The present invention advantageously employs an earlier disclosed method for amplification and affinity modification of the target nucleic acid to be detected. In the present method the target nucleic acid containing the variable nucleotide(s) is immobilized on a solid support permitting the removal of the amplification mixture from the target nucleic acid.

The present invention also encompasses individual primer reagents and reagent combinations or kits for practising the method of the invention. While the precise reagents and packaging will depend on the type of nucleotide variations or point mutations to be detected, such a kit will in general include at least one modified amplification primer having an attachment moiety included and at least one detection step primer, but may also include at least one support adapted to immobilize the modified copies of the target nucleic acid and at least one labelled nucleoside triphosphate.

BRIEF DESCRIPTION OF THE DRAWINGS

FIG. 1 illustrates a set-up for a test according to the disclosed method in the case where one variable nucleotide residue (X1 or X2) is detected.

FIG. 2 illustrates a set-up for a test according to the disclosed method in which case the detection step primer is chosen to span the nucleotide sequence n nucleotides from the variable nucleotide to be detected.

Figure 3:
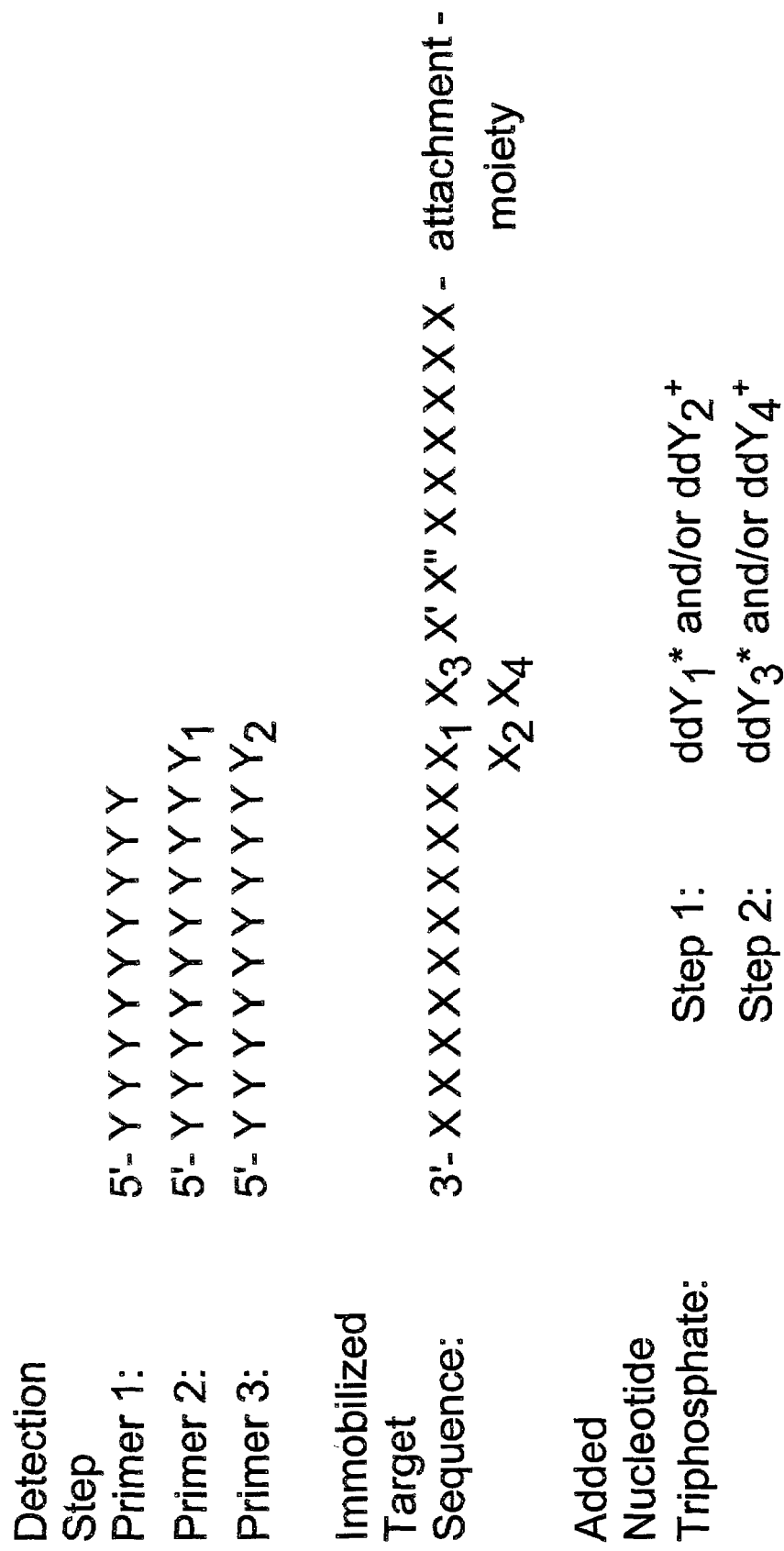
FIG. 3 illustrates a set-up for a test according to the disclosed method, in a case where a plurality of mismatches adjacent to each other, is to be detected. In this case the test is performed in two steps, whereby the detection step primer 1 is eluted before step two is performed.

Symbols Used in the Figures:
X and X' denote nucleotide residues
The variable nucleotide to be detected is denoted either X1, X2, X3 or X4
Y1, Y2, Y3 and Y4 denote nucleotides complementary to X1, X2, X3 or X4, respectively
dY denotes a deoxyribonucleoside triphosphate
dY* and dY+ denote labelled deoxyribonucleoside triphosphates
ddY denotes a dideoxyribonucleoside triphosphate
ddY* and ddY+ denote labelled dideoxyribonucleoside triphosphates
* and + denote different detectable labels

DETAILED DESCRIPTION OF THE INVENTION

The present invention resides in a method to determine a specific nucleotide variation in a previously defined region of a nucleic acid present in a complex nucleic acid mixture. This defined region containing the nucleotide variation is herein referred to as the "target nucleic acid".

The method according to the invention is based on a primer extension reaction, using at least one detection step primer complementary to the nucleotide sequence 3' from the variable nucleotide to be detected. The detection of the variable nucleotide is performed by detecting a labelled nucleoside triphosphate incorporated by extension of the detection step primer.

Preferably the target nucleic acid is amplified in vitro prior to the detection step to provide a detectable amount of the target nucleic acid. The actual quantity of nucleic acid will vary depending on the labeling moiety employed in the detection step and the sensitivity of analytical techniques for that moiety. In a preferred method according to the present invention, an affinity moiety is introduced into copies of the region of interest of the target nucleic acid. This is conveniently done by a primer dependent amplification reaction using at least one affinity labelled amplification primer. The copies of the target nucleic acid molecules are immobilized on a solid support with the aid of the introduced affinity moiety.

Different set-ups of the test are described below in the description of the preferred embodiments and further illustrated by the examples. It will be evident to one skilled in the art, that the possibilities of constructing the test are not limited to these given examples and that the set-up of the test is determined by the given mutation or nucleotide variation to be detected.

(a) Introduction of Affinity Moieties Into Copies of the Target DNA

The source of the target nucleic acid (DNA or RNA) suspected to contain the variable nucleotide residue can be any human, animal or plant cell or a microbe. The target nucleic acid can be isolated from biological samples by conventional nucleic acid purification methods, but according to the present invention it is possible to use crude biological samples.

The target nucleic acid comprising the variable nucleotide site of interest is preferably multiplied in vitro using one or more primers close to the nucleotide sequence of interest. The term "amplification" as used herein refers to any primer dependent elongation of a nucleotide sequence with the aid of a polymerizing agent. Suitable primer dependent elongation reactions are for example the polymerase chain reaction (Kleppe et al., 1971, J. Mol. Biol., 56:341–361; and U.S. Pat. No. 4,683,202), processes utilizing both primer dependent replication and independent transcription (European Patent Publication EP-329822) or ligation amplification reactions (PCT Patent Publication WO-89/09835).

We have previously developed a convenient method of nucleotide sequencing, which is well adapted for use as a routine diagnostic tool (U.S. patent application Ser. No. 277,643, which is hereby incorporated by reference). This method makes use of the affinity based hybrid collection method disclosed in U.S. patent application Ser. No. 024,604, incorporated herein by reference. Preferably the target DNA to be tested is amplified in vitro prior to sequencing. In this method one of the primers used in the amplification reaction comprises an attachment moiety such as biotin. The enriched fragment is captured on a solid matrix, to which streptavidin or avidin has been attached. The excess reagents are completely removed by washing the matrix. The captured fragment is rendered single stranded and the chain termination reactions are carried out directly on the matrix. The products of the chain termination reaction are released and the nucleotide sequence is determined after polyacrylamide gel electrophoresis. This diagnostically suitable solid phase sequencing method provides several advantages over the prior art methods for determining nucleotide variations described above, but still contains the laborious, expensive and skill-requiring sequencing gel electrophoresis step.

According to the present invention the amplification of the target nucleic acid comprising the suspected nucleotide variation is conveniently done by using a modified primer introducing affinity moieties into the copies of the target nucleic acid sequence. In such an amplification, one or both of the amplification primers are modified to include attachment moieties. By selecting which amplification primer is modified, it is possible to determine which strand of a double stranded DNA the variable site is detected on. The target sequence of interest is preferably amplified with a suitable number of cycles of this modified polymerase chain reaction.

As a result of this process, copies of the original target nucleic acid sequence, now modified with attachment moieties, are obtained by incorporation of the modified primers into the synthesized polynucleotide molecules.

The term "attachment moiety" as used herein refers to any component having affinity for another component which forms an affinity pair with that other component. For example, biotin-avidin/streptavidin, antigens or haptens-antibodies, heavy metal derivatives-thiogroups, various polynucleotides such as homopolynucleotides as poly dG-poly dC, poly dA-poly dT and poly dA-poly U, are such affinity pairs. Any component pairs with strong affinity for each other can be used as the affinity pair. Suitable affinity pairs are also found among ligands and conjugates used in immunological methods. An "attachment moiety" is an affinity moiety or a moiety providing a site for the attachment of an affinity moiety.

The term "modified amplification primer" as used herein refers to an oligonucleotide primer modified so as to contain an attachment moiety. The oligonucleotide primers may be synthesized by standard chemical methods or prepared by recombinant DNA techniques. The essential feature of the amplification primer is that it is able to specifically bind by base pairing to the original target nucleotide sequence of interest at a point in the sequence such that the site of interest will be amplified. Thus the amplification must be complementary to a region of the target nucleotide sequence between the 3' end of the target nucleic acid and the site of interest. The 3' end of the amplification primer is preferably complementary to the target nucleic acid sequence at a point less than 100 residues removed from the site of interest due to limitations in polymerase enzyme processivity. The size of the primers is preferably between 14 and 40 bases, but primers as short as 8 bases or considerably longer than 40 bases may be used. The primers are modified with the attachment moieties using chemical or enzymatic or any other method. Preferably the attachment moiety is attached to the 5' end of the primer. Other sites of attachment are also possible, provided that the base pairing property of the primer and its ability to function in an elongation reaction are retained.

(b) Separation of the Target Nucleic Acid Copies.

After amplification, the target nucleic acid copies are separated from the amplification mixture. In the preferred method of the invention, copies of the target nucleic acid molecules containing the attachment moieties are immobilized on a solid matrix with the aid of a complementary attachment site, e.g. the other component of the affinity pair. The matrix is then washed to remove all unbound material, such as nucleotide triphosphates and primers, that could interfere with the reactions during the detection step. The immobilized target nucleic acid is rendered single-stranded either before or after the immobilization step. The immobilization of the modified target nucleic acid copies makes it possible to reuse the target sequence if multiple determinations are to be performed on the same target sequence of interest.

The term "solid matrix" as used herein refers to any format, such as beads, microparticles, the surface of a microtitration well or a test tube, a dipstick or a filter. The material of the matrix may be polystyrene, cellulose, latex, nitrocellulose, nylon, polyacrylamide, dextran or agarose. The only prerequisite for the material is that the attachment site can be attached to it.

(c) The Detection Step Primer

After separation from the amplification mixture, the single-stranded DNA fragment is allowed to hybridize to a primer, the detection step primer, which is complementary to the nucleotide sequence 3' of the variable nucleotide. This can be carried out in an immobilized state or in solution.

The term "detection step primer" as used herein refers to an oligo- or polynucleotide primer, which functions as the point of initiation for the primer dependent elongation. The detection step primer is selected as to be hybridizable to a nucleotide sequence immediately or closely adjacent to the variable nucleotide to be detected. The detection step primer can be chosen so as to be complementary to either the coding or the non-coding strand of a double stranded target, depending on which strand was immobilized in step (b) described above. The detection step primer can be modified, e.g. with an affinity moiety as described in section a) above but using a different affinity moiety. Preferably the detection step primer is not modified.

The selection of the detection step primers is determined by the nature of the nucleotide variation to be detected.

In a preferred embodiment of the method according to the present invention, the detection step primer is selected as to be immediately adjacent to the variable nucleotide to be detected.

In another embodiment of the method according to the present invention the detection step primer is selected to be hybridizable to a nucleotide sequence n nucleotide residues away from the variable nucleotide to be detected. The only limitation as to the number n of nucleotide residues between the 3' end of the detection step primer and the variable nucleotide is that there must be no nucleotide residues identical to the one(s) to be detected among these n nucleotide residues.

In another embodiment of the method according to the present invention two or more variable nucleotide residues are identified. In this case it is necessary to design at least two different detection step primers.

The set-up of the test depending on the nucleotide variations to be detected are further described below.

(d) The Detection Step Primer Extension

The detection step primer is annealed to the copies of the target nucleic acid and a solution containing one or more nucleoside triphosphates including at least one labelled or modified nucleoside triphosphate, is added together with a polymerizing agent in conditions favoring primer extension. Either labelled deoxyribonucleoside triphosphates (dNTPs) or chain terminating dideoxyribonucleoside triphosphates (ddNTPs) can be used. The polymerizing agent will extend the primer with the nucleoside triphosphate complementary to the variable nucleotide adjacent to the primer. The extended nucleic acid may be immobilized during this detection step primer extension, for example, via affinity-binding of a modified amplified copy, or it may be immobilized afterwards, for example, via an affinity-modified detector primer. In either case, after washing the affinity-matrix, the incorporated label is measured directly on the matrix or after elution.

The term "labelled nucleoside triphosphate" as used herein refers to any nucleoside triphosphate, deoxy- or dideoxyribonucleosidetriphosphate, labelled with a detectable label or modified so as to comprise an attachment moiety capable of binding a detectable label. The method according to the invention is not dependent on the label used, although sensitivity will vary depending on the detectability of the label. The only limitation as to the choice of the detectable label is that it will not disturb the incorporation of the labelled nucleoside triphosphate during the polymerization reaction.

The term "polymerizing agent" as used herein refers to any enzyme which is capable of primer dependent elongation of nucleic acids. Suitable enzymes include, for example, T7 DNA polymerase, T4 DNA polymerase, the Klenow fragment of *Escherichia coli* DNA polymerase and other suitable DNA polymerases, reverse transcriptase and polymerases from thermophilic microbes such as *Thermus aquaticus* and *Thermus thermophilus*.

(e) Preferred Modes of Detecting Nucleotide Variations

FIG. 1 illustrates schematically an embodiment of the invention. The target nucleic acid is represented by X's, with X1 and X2 representing two alternative nucleotide residues at the site to be investigated. The detection step primer illustrated in FIG. 1 is represented by Y's, and is complementary to the portion of the target sequence starting immediately 3'-ward of the site to be investigated. In practising the invention the detection step primer is hybridized to the target sequence, and a selected nucleoside triphosphate or a mixture of nucleoside triphosphates is added and a chain extension reaction is allowed to proceed under conditions favorable for elongation of the primer.

In the simplest embodiment of the invention, the nucleoside triphosphate mixture contains just the labelled dideoxynucleoside triphosphate (ddNTP) corresponding to either X1 or X2 (option a in FIG. 1). The incorporation of a ddNTP terminates the primer extension reaction after the incorporation of only this one nucleotide, whereafter it is possible to determine the variable nucleotide by detecting the incorporated label of the added nucleotide.

This embodiment is especially suitable when the nucleotide variation to be detected consists of one single point mutation (X1→X2). The sample can be divided into two parts, whereafter X1 is detected from one of the samples and X2 from the other. This allows the identification of heterozygous samples. It is equally possible to add two or more different and differently labelled ddNTPs to an undivided sample (option b in FIG. 1). In this embodiment it is possible to determine more than one point mutation occurring at the same site out of one undivided sample (X1→X2, X3 or X4).

It is also possible to use a labelled deoxynucleoside triphosphate (dNTP), which corresponds to the variable nucleotide to be detected and to determine the incorporation of this label. When a labelled dNTP is used, it is advantageous, but not necessary, to add unlabelled ddNTPs corresponding to the other three nucleotide residues (option c in FIG. 1). The addition of chain terminating ddNTPs provides a means for preventing incorporation of possibly remaining NTPs from the modification step (a).

Yet another possibility is to use two or more different, differently labelled dNTPs making it possible to detect heterozygotes in an undivided sample. When using more than one labelled dNTP the results may be difficult to interpret if the nucleotide residue x following the variable nucleotide residue in the target sequence is identical to either of the added ones (option d in FIG. 1).

FIG. 2 illustrates schematically another embodiment of the invention. The detection step primer in FIG. 2 is complementary to a portion of the target sequence starting n nucleotide residues away from the variable nucleotide to be detected. The only limitation as to the number n of nucleotide residues between the 3' end of the detection step primer and the variable nucleotide is that there must be no nucleotide residues identical to the one(s) to be detected among these n nucleotide residues. In this case the added nucleoside triphosphates comprise unlabelled dNTPs complementary to the n nucleotides between the primer and the variable nucleotide and at least one labelled nucleoside triphosphate depending on the nucleotide variation to be detected. Two or more differently labelled ddNTPs can of course be used as earlier described in the embodiments illustrated by FIG. 1 options b and d.

FIG. 3 illustrates schematically yet another embodiment of the method according to the present invention where two or more variable nucleotide residues are identified. In this case it is necessary to design at least two different detection step primers. The first primer is selected so as to be complementary to the nucleotide sequence starting immediately adjacent to the first variable nucleotide residue (primer 1 in FIG. 3). Furthermore one or two detection primers are employed spanning also the first variable nucleotide residue detected by primer 1. The test can be performed by dividing the sample into two, whereby primer 1 is added to sample 1 to identify the first variable nucleotide residue. The two other primers (primers 2 and 3 in FIG. 3) are added to sample 2 to detect the second variable nucleotide. Due to the immobilization of the target nucleic acid sequence, the identification of two or more subsequent variable nucleotides can be identified from one single undivided sample, by performing the aforementioned detection steps sequentially and including an elution step after the detection of the first variable nucleotide to remove primer 1.

Reagents for use in practising the method of the invention may be provided individually or may be packaged in kit form. For example, kits might be prepared comprising one or more detection step primers and one or more labelled nucleoside triphosphates, preferably comprising also packaged combinations of one or more affinity labelled amplification primers and corresponding solid support(s).

The arrangement of the reagents within containers of the kit will depend on the specific reagents involved. Each reagent can be packaged in an individual container, but various combinations may also be possible.

The present invention is illustrated with the following examples, which are not intended to limit the scope of the invention.

EXAMPLE 1

Identification of the apolipoprotein E polymorphism in the codons for amino acid residues 112 and 158 using [$^{35}$S] as label

Synthesis of Oligonucleotides

Four PCR primers (P1–P4) and two detection step oligonucleotide primers (D1 and D2) were synthesized on an Applied Biosystems 381A DNA synthesizer. The nucleotide sequence of the oligonucleotides, and their location (given as nucleotide numbers) on the apolipoprotein E gene (Apo E) were:

```
P1: 5'-AAG GAG TTG AAG GCC TAC AAA T    (3616–3637)

P3: 5'-GAA CAA CTG AGC CCG GTG GCG G    (3649–3670)

D1: 5'-GCG CGG ACA TGG AGG ACG TG       (3725–3744)

D2: 5'-ATG CCG ATG ACC TGC AGA AG       (3863–3882)

P2: 5'-TCG CGG GCC CCG GCC TGG TAC A    (3914–3893)

P4: 5'-GGA TGG CGC TGA GGC CGC GCT C    (3943–3922)
```

A 5'-aminogroup was added to the primer P2 with the aminolink II reagent (Applied Biosystems). The amino group was biotinylated using sulfo-NHS-biotin (Pierce Chemical Co.) and purified by reverse phase HPLC.

The DNA Samples

Venous blood samples were obtained from patients of known Apo E phenotype attending the Lipid Outpatient Clinic of the University Central Hospital of Helsinki, Finland. Leukocytic DNA was extracted according to standard procedures.

Polymerase Chain Reaction-Amplification

The DNA (100 ng per sample) was amplified with the P1 and P4 primers (final concentration 1 µM) in 100 µl of a solution of 0.2 mM each of dATP, dCTP, dGTP, dTTP, 20 mM Tris-HCl, pH 8.8, 15 mM (NH$_4$)$_2$SO$_4$, 1.5 mM MgCl$_2$, 0.1% Tween 20, 0.1 mg/ml gelatin and 2.5 units of *Thermus aguaticus* DNA-polymerase (United States Biochemical Corp.) in a DNA thermal cycler (Perkin-Elmer/Cetus) for 25 cycles of 1 min. at 96° C. and 2 min. at 65° C. An aliquot (3 µl of a 1:100 dilution) of this first PCR amplification mixture was transferred to a second PCR. This was carried out at the conditions described above and directed by the biotinylated primer P2 and the primer P3.

Affinity-Capture of the Biotinylated Amplified Apo E DNA on Avidin-Coated Polystyrene Particles Five µl of a 5% (w/v) suspension of avidin-coated polystyrene particles (0.8 µm, Baxter Healthcare Corp.) were added to an 80 µl aliquot of the second amplification mixture. The samples were kept at 20° C. for 30 min. The particles were collected by centrifugation for 2 min. in an Eppendorf centrifuge and were washed once by vortexing with 1 ml of 15 mM NaCl, 1.5 mM Na-citrate (0.1×SSC), 0.2% sodium dodecyl sulphate (SDS), and once with 1 ml of 0.1% Tween 20 in 0.15 M NaCl, 20 mM phosphate buffer, pH 7.5 (PBS). The particles were treated twice with 200 µl of 0.15 M NaOH for 5 min. at 20° C. The particles were then washed once with 1 ml of 0.1% Tween 20 in 50 mM NaCl, 40 mM Tris-HCl, pH 7.5 and twice with 1 ml of 0.01% Tween 20 in 50 mM NaCl, 40 mM Tris-HCl, pH 7.5. The suspension of particles in the last washing solution was divided into four parts, and the particles were collected by centrifugation in separate tubes.

Identification of the Variable Nucleotides

The particles carrying the DNA fragment were suspended in 10 µl of 50 mM NaCl, 20 mM MgCl$_2$, 40 mM Tris-HCl, pH 7.5, containing 2 pmol of the detection step primer. The D1 oligonucleotide located immediately adjacent to the variable nucleotide number 3745 (codon 112, T or C,) was added to two of the tubes and the D2 oligonucleotide adjacent to the variable nucleotide number 3883 (codon 158, T or C) to two tubes. The oligonucleotide was annealed to the DNA template by heating the samples at 65° C. for 2 min. and allowing them to cool to 20° C. One µl of 0.1 M dithiothreitol (DTT) and [$^{35}$S]-labelled deoxynucleoside triphosphates (dNTP) and dideoxynucleoside triphosphates (ddNTP) were added to yield 1 µM concentrations each in a final volume of 15 µl as follows:

for identification of T: [$^{35}$S]-dTTP (Amersham), ddCTP and ddGTP to two tubes, one in which the oligonucleotide D1 and one in which the oligonucleotide D2 had been annealed.

for identification of C: [$^{35}$S]-dCTP (Amersham), ddTTP, and ddGTP to two tubes, one in which the oligonucleotide D1 and one in which the oligonucleotide D2 had been annealed.

Two µl (3U) of T7 DNA polymerase (Sequenase™, United States Biochemical Corp.) was added to each tube and the reaction was allowed to proceed for 6 min. at 42° C. The microparticles were washed at 20° C. by vortexing twice with 1 ml of 0.1×SSC, 0.2% SDS and twice with 0.1% Tween 20 in PBS. For elution of the reaction products the particles were boiled in 200 µl of H$_2$O for 5 min., cooled on ice and centrifuged for 2 min. in an Eppendorf centrifuge. The eluted radioactivity was measured in a liquid scintillation counter. The result of an experiment where four samples of the phenotypes E2/E2 (T/T in codon 112, T/T in codon 158), E4/E3 (T/C in codon 112, C/C in codon 158), E2/E3 (T/T in codon 112, T/C in codon 158) and E4/E4 (C/C in codon 112, C/C in codon 158) were analyzed as described above is presented in the following table:

| Sample No. | Phenotype | Detector (codon) | Radioactivity eluted (cpm) T-reaction | C-reaction | Result |
|---|---|---|---|---|---|
| 1. | E2/E2 | D1 (112) | 18400 | 625 | T/T |
| 2. | E4/E3 | D1 (112) | 73700 | 58100 | T/C |
| 3. | E2/E3 | D1 (112) | 112000 | 1360 | T/T |
| 4. | E4/E4 | D1 (112) | 2310 | 99700 | C/C |
| 5. | No DNA | D1 (112) | 429 | 1195 | |
| 1. | E2/E2 | D2 (158) | 67000 | 7000 | T/T |
| 2. | E4/E3 | D2 (158) | 3220 | 35100 | C/C |
| 3. | E2/E3 | D2 (158) | 44600 | 26400 | T/C |
| 4. | E4/E4 | D2 (158) | 1485 | 19300 | C/C |
| 5. | No DNA | D2 (158) | 686 | 760 | |

Conclusion

The differences in cpm values obtained in the T- and C-reactions allowed unequivocal identification of the variable nucleotide in both codon 112 and codon 158 in all four DNA samples.

The variable nucleotide can optionally be determined as described above, but performing the second PCR with biotinylated primer P3 and primer P2. As detection step primers are then used primers complementary to the opposite strand of the ApoE gene:

D4: 5'-GTA CTG CAC CAG GCG GCC GC (3765-3746)
D5: 5'-GGC CTG GTA CAC TGC CAG GC (3903-3884)

EXAMPLE 2

Identification of the variable nucleotide in codon 112 of the apolipoprotein E gene using double labelling ([$^3$H] and [$^{32}$P]) in one reaction.

Oligonucleotides and DNA Samples

The PCR primers P1, biotinylated P2, P3 and P4, and the detection step primer D1 described in Example 1 were used in this example. The DNA was extracted from blood samples as described in Example 1.

Polymerase Chain Reaction-Amplification and Affinity-Capture

The PCR amplification and the affinity-capture of the amplified fragments were carried out as described in Example 1. In the last washing step each sample was divided into two aliquots.

Identification of the Variable Nucleotide at Codon 112

The particles were suspended in 10 µl of buffer (see Example 1) containing 2 pmol of the detection step primer D1, which hybridizes immediately 3' to the variable nucleotide in codon 112. The annealing reaction was carried out as in Example 1. One µl of 0.1 M DTT was added.

The identification of the variable nucleotide (C or T) was now done by adding [$^3$H]- and [$^{32}$P]-labelled dNTPs simultaneously to one sample. Either [$^3$H]-dCTP and [$^{32}$P]-dTTP or [$^3$H]-dTTP and [$^{32}$P]-dCTP (Amersham) were used. The [$^3$H]-dNTPS were added to 1 µM concentrations. The [$^{32}$P]-dNTPs were diluted in unlabelled dNTP to yield 1 µM final concentrations and specific activities similar to those of the [$^3$H]-dNTPs. All reactions contained 1 µM ddGTP. The final volume was 15 µl. Three units of T7 DNA polymerase was added, and the labelling and washing procedures were carried out as in Example 1. The eluted, [$^3$H] and [$^{32}$P] radio-activity in each sample was measured simultaneously in a Rackbeta 1219 scintillation counter (Pharmacia/Wallac) by setting the window for [$^3$H] at channels 10–90 and the windows for [$^{32}$P] at channels 130–220.

The table below shows the result of an experiment, in which three samples, one of the phenotype E2/E3 (T/T in codon 112), one of the phenotype E4/E4 (C/C in codon 112) and one of the phenotype E3/E4 (T/C on codon 112) were analyzed either using [$^3$H]-dCTP and [$^{32}$P]-dTTP or using [$^3$H]-dTTP and [$^{32}$P]-dCTP:

| Sample | Labelled dNTPs | Radioactivity eluted (cpm) $^3$H Ch.10–90 | $^{32}$P Ch.130–220 |
|---|---|---|---|
| E2/E3 | [$^3$H]dCTP / [$^{32}$P]dTTP | 502 | 7870 |
| E4/E4 | [$^3$H]dCTP / [$^{32}$P]dTTP | 6070 | 186 |
| E3/E4 | [$^3$H]dCTP / [$^{32}$P]dTTP | 5120 | 5980 |
| No DNA | [$^3$H]dCTP / [$^{32}$P]dTTP | 172 | 148 |
| E2/E3 | [$^3$H]dTTP / [$^{32}$P]dCTP | 10800 | 183 |
| E4/E4 | [$^3$H]dTTP / [$^{32}$P]dCTP | 394 | 4932 |
| E3/E4 | [$^3$H]dTTP / [$^{32}$P]dCTP | 7800 | 5140 |
| No DNA | [$^3$H]dTTP / [$^{32}$P]dCTP | 175 | 44 |

Conclusion

The signals obtained allowed the identification of the variable nucleotide in codon 112 from undivided samples using two dNTPs carrying different labels. In this example only half of each sample was analyzed per reaction. Thus the other half of the sample can be used to analyze the nucleotide variation in codon 158 of the Apo E gene.

EXAMPLE 3

Identification of the variable nucleotide in codon 158 of the apolipoprotein E gene after a single polymerase chain reaction amplification.

Oligonucleotides and DNA Samples

In this example the biotinylated primer P2 and the primer P3 were used in the PCR amplification. The detection step primer was D2 (see Example 1). The DNA was extracted from venous blood as described in Example 1.

Polymerase Chain Reaction-Amplification and Affinity-Capture

The DNA (100 ng per sample) was amplified with the biotinylated P2 and the P3 primer (final concentration 1 μM) at the conditions described in Example 1 with the following exception: Only one amplification process consisting of 30 cycles of 1 min. at 96° C., 1 min. at 55° C. and 1 min. 72° C. was carried out.

The affinity-capture on avidin-coated polystyrene particles was done as in Example 1. Each sample was divided into two parts in the last washing step.

Identification of the Variable Nucleotide in Codon 158

The particles were suspended in 10 μl of buffer (see Example 1) containing 2 pmol of the detection step primer D2, which hybridizes immediately 3' of the variable nucleotide in codon 158. The annealing reaction was as in Example 1. One μl of 0.1 M DTT was added. [$^{35}$S]-labelled dNTPs and ddNTPs were added to the T- and C-reactions as specified in Example 1. The primer extension reaction, the washing procedure and the elution of the bound radioactivity was done as described in Example 1.

Three samples with the phenotypes E2/E2 (T/T in codon 158), E2/E3 (T/C in codon 158) and E4/E3 (C/C in codon 158), respectively, were analyzed. The results of this experiment is presented in the table below:

|        | Radioactivity eluted (cpm) | |        |
| ------ | ---------- | ---------- | ------ |
| Sample | T-reaction | C-reaction | Result |
| E2/E2  | 64600      | 7746       | T/T    |
| E2/E3  | 39600      | 22700      | T/C    |
| E4/E3  | 5640       | 53500      | C/C    |
| No DNA | 1325       | 1910       |        |

Conclusion

The method allowed correct identification of the variable nucleotide at position 158 also when the apo E DNA fragment was enriched by a single PCR with one primer pair.

EXAMPLE 4

Identification of the variable nucleotide in codon 112 of the apolipoprotein E gene with enzymatic detection.

Oligonucleotides and DNA Samples

The PCR primers P1, biotinylated P2, P3 and P4, and the detection step primer D1 described in Example 1 were used. The DNA was extracted from blood samples as described in Example 1.

Polymerase Chain Reaction-Amplification

The DNA (100 ng per sample) was amplified with the primers P1 and P4 at 1 μM concentration as described in example 1. Three μl of a 1:100 dilution of this first PCR mixture was reamplified using the biotinylated P2 and the P3 primer at 0.1 μM concentration. The second PCR was carried out for 30 cycles of 1 min. at 96° C., 1 min. at 55° C. and 1 min. at 72° C.

Affinity-Capture of the Amplified DNA in Avidin-Coated Microtitration Wells

Two 15 μl aliquots per sample of the second PCR mixture were transferred to microtitration wells (Nunc, Maxisorb), that had been coated with streptavidin by passive absorption. 30 μl of 0.1% Tween 20 in 0.15 M NaCl, 0.1 M Tris-HCl, pH 7.5 (TBS) was added to each well. The microtitration strips were incubated for 3 hours at 37° C. with gentle shaking. The wells were washed three times with 200 μl of 0.1% Tween 20 in TBS at 20° C. The wells were then treated twice with 100 μl of 50 mM NaOH for 5 min. at 20° C. followed by washing twice with 200 μl of 0.1×SSC, 0.2% SDS, twice with 0.1% Tween 20 in TBS, once with 0.1% Tween 20 in 50 mM NaCl, 40 mM Tris-HCl, pH 7.5, and finally once with 0.01% Tween 20 in 50 mM NaCl, 40 mM Tris-HCl, pH 7.5.

Identification of the Variable Nucleotide

Ten pmol of the oligonucleotide D1 was added to each well in 50 μl of 0.9 M NaCl, 0.2 M Tris-HCl, pH 7.5. The wells were heated at 65° C. for 2 min. and allowed to cool slowly to 20° C. The mixture was discarded and the wells were washed once with 200 μl of 0.25 M NaCl, 0.2 M Tris-HCl, pH 7.5 at 20° C. 50 μl of a solution consisting of 1 μM digoxigenin-11-dUTP (Boehringer-Mannheim), 1 μM ddCTP, 1 μM ddGTP, 0.2 μM oligonucleotide D1, 6 mM DTT, 37.5 mM NaCl, 15 MM MgCl$_2$, 30 mM Tris-HCl, pH 7.5 and 3 units of T7 DNA polymerase was added. The microtitration strips were incubated at 42° C. for 10 min. and the wells were washed twice with 200 μl of 0.1×SSC, 0.2% SDS, and three times with 200 μl of 0.1% Tween 20 in TBS. Then 60 μl of a 1:500 dilution of an anti-digoxigenin-alkaline phosphatase conjugate (Boehringer-Mannheim) in a solution of 0.1% Tween 20, 1% bovine serum albumin in TBS was added, and the microtitration strips were incubated at 37° C. for 2 hours with gentle shaking. The wells were washed six times with 0.1% Tween 20 in TBS and once with 1 M diethanolamine-0.5 M MgCl$_2$ buffer, pH 10. Finally 60 μl of 2 mg/ml p-nitrophenyl phosphate in the alkaline buffer was added. After development of color for 20 min. at room temperature, 100 μl of the alkaline buffer was added and the absorbance of the formed product was measured at 405 nm in a spectrophotometric reader.

Two samples with the phenotypes E2/E2 (T/T in codon 112) and E4/E4 (C/C in codon 112) were analyzed. The result of this experiment is presented in the table below:

| Sample | Absorbance at 405 nm (duplicate samples) | | Result |
|---|---|---|---|
| E2/E2 | 1.180 | 0.707 | T/T |
| E4/E4 | 0.040 | 0.010 | C/C |
| No DNA | 0.025 | 0.010 | |

Conclusion

The variable nucleotide in codon 112 was identified after incorporation of digoxigenin-11-dUTP and subsequent detection with an antibody labelled with alkaline phosphatase.

EXAMPLE 5

Identification of the Apolipoprotein E Polymorphism in the Codon for Amino Acid Residue 112 Using Fluorescent Label Oligonucleotides and DNA Samples The PCR primers P1, biotinylated P2, P3 and P4, and the detection step primer D1 described in Example 1 are used. The DNA is extracted from blood samples as described in Example 1.

Polymerase Chain Reaction-Amplification and Affinity-Capture

The DNA (100 ng per sample) is amplified with the primers P1 and P4 at 1 μM concentration as described in Example 1. Three μl of a 1:100 dilution of this first PCR mixture is reamplified using the biotinylated P2 and the P3 primer at 1 μM concentration. The second PCR is carried out for 25 cycles of 1 min. at 96° C., 1 min. at 55° C. and 1 min. at 72° C. The biotinylated amplified DNA fragments are captured on avidin-coated polystyrene particles as in Example 1. Each sample is divided into two parts in the last washing step.

Identification of the Variable Nucleotide in Codon 112

The particles carrying the amplified DNA are suspended in 10 μl of buffer (see Example 1) containing 5 pmol of the detection step primer which hybridizes immediately 3' of the variable nucleotide in codon 112. The annealing reaction is carried out as in Example 1. One μl of 0.1 M DTT is added to each tube. For identification of T, 400 pm of fluorescent ddTTP (T-terminator; DuPont, NEK-528T) is added to one of the tubes. For identification of C, 40 pm of fluorescent ddCTP (C-terminator; DuPont, NEK-519C) is added to the other tube. Five units of T7 DNA polymerase is added to both tubes to a final reaction volume of 15 μl. The reaction is allowed to proceed for 5 min. at 37° C. The particles are washed as described in Example 1 and the reaction products are eluted. The fluorescence of the eluant is measured in a fluorescence spectrophotometer (Merck/Hitachi, F-1000) using 490 nm as the excitation wavelength and 550 nm for measurement of the emitted fluorescence.

Interpretation of the Result

A positive signal from only the T-reaction shows that the subject is homozygous for a cysteine residue at position 112. A positive signal from only the C-reaction shows that the subject is homozygous for an arginine residue at position 112. Positive signals from both reactions show that the subject is heterozygous, i.e. has one allele with a cysteine residue, and one allele with an arginine residue at position 112 of the apolipoprotein E gene.

EXAMPLE 6

Detection of the Sickle Cell Mutation in the Sequence Encoding Codon 6 of the Human β-Globin Gene Synthesis of Oligonucleotides The PCR primers are designed to contain 3' ends that are mismatched to the otherwise strongly homologous β-globin gene. Two PCR primers, denoted B1 and B2, and one detection step primer B3, are synthesized by the method described in Example 1. The primer B2 is biotinylated as described in Example 1. The nucleotide sequence of the oligonucleotides and their location on the β-globin gene (as nucleotide numbers relative to the transcription initiation site) are the following:

```
B1: 5'-CAT TTG CTT CTG ACA CAA CT    (-49—30)

B3: 5'-CAT GGT GCA CCT GAC TCC TG    (-1—19)

B2: 5'-CAA CTT CAT CCA CGT TCA CC    (73-54).
```

Polymerase Chain Reaction-Amplification and Affinity-Capture

The DNA is extracted from blood samples as described in Example 1. The DNA (100 ng per sample) is amplified with the primers B1 and biotinylated B2 as described in Example 3. The biotinylated amplified DNA fragments are captured on avidin-coated polystyrene particles as in Example 1. Each immobilized sample is divided into two parts.

Identification of the A→T Mutation in Codon 6

The particles carrying the amplified DNA sample are suspended in 10 μl of buffer (see Example 1) containing 2 pmol of the B3 detection step primer, which hybridizes immediately 3' of the mutation site in codon 6. The annealing reaction is carried out as in Example 1. One μl of 0.1 M DTT is added. [$^{35}$S]-labelled dNTPs and ddNTPs are added to yield 0.2 μM concentrations in a final volume of 15 μl as follows:—for identification of the normal allele (A): [$^{35}$S]-dATP, ddTTP, ddGTP to one of the tubes—for identification of the mutation (T): [$^{35}$S]-dTTP, ddATP, ddGTP to the other tube.

One unit of T7 DNA polymerase is added, and the reaction is allowed to proceed for 5 min. at 37° C. The particles are washed, the reaction products are eluted and the eluted radioactivity is measured in a scintillation counter as described in Example 1.

Interpretation of the Result

A positive signal from only the A-reaction shows that the subject is homozygous and normal. A positive signal from only the T-reaction shows that the subject is homozygous for the sickle cell mutation. A positive signal from both reactions shows that the subject carries the sickle cell mutation in one allele i.e. is heterozygous.

The variable nucleotide can optionally be determined as described above, but performing the PCR with biotinylated primer B1 and primer B2. A primer complementary to the opposite strand of the β-globin gene is then used as detection step primer:

B4: 5'-CAG TAA CGG CAG GCG GCC GC (40–21)

EXAMPLE 7

Detection of Point Mutations in the Sequence Encoding Codon 12 in the K-Ras Gene

Synthesis of Oligonucleotides

Two PCR primers, denoted R1 and R2, respectively, are synthesized and the primer R1 is biotinylated as described in Example 1. For detection of a mutation of the glycine residue (encoded by GGT) in position 12, two detection step primers, R3 and R4, are synthesized. R3 is used to detect a mutated G in the second position and R4 to detect a mutated G in the first position of codon 12. The sequence and position (as nucleotide numbers) of the oligonucleotides on the first exon of the K-ras gene is given below:

```
R1: 5'-ATG ACT GAA TAT AAA CTT GTG    (1-20)

R2: 5'-TTC GTC CAC AAA ATG ATT CTG    (94-74)

R3: 5'-AAG GCA CTC TTG CCT ACG CCA    (56-36)

R4: 5'-AGG CAC TCT TGC CTA CGC CAC    (55-35)
```

Polymerase Chain Reaction-Amplification, Affinity-Capture and Annealing of the Detection Step Primers The DNA is extracted from tumor cell samples by standard methods using digestion with proteinase K, phenol extraction and precipitation with ethanol. 100 ng of the purified DNA is amplified with the biotinylated primer R1 and the primer R2 using the conditions described in Example 3, except that the primer annealing temperature is 50° C. The amplified DNA is captured on avidin-coated polystyrene particles, denatured and the particles are washed as described in Example 1. The immobilized DNA sample is divided into two tubes. The particles in one of the tubes are suspended in 10 µl of buffer (see Example 1) containing 2 pmol of the oligonucleotide R3, which will anneal immediately 3' of the C complementary to the second G in codon 12. In the other tube 10 µl of buffer containing 2 pmol of the oligonucleotide R4 annealing 3' to the C complementary to the first G in codon 12 is used. The annealing reaction is carried out as in Example 1. One µl of 0.1 M DTT is added. The mutation in codon 12 is analyzed according to method A or method B below.

A. Identification of a Gly—Non-Gly Mutation in Codon 12

A mixture of [$^{35}$S]-dATP, [$^{35}$S]-dGTP, [$^{35}$S]dTTP and ddCTP are added to both tubes to give a final concentration of 1 µM each in 15 µl. One unit of T7 DNA polymerase is added and the reaction is allowed to proceed for 5 min. at 37° C. The particles are washed, the reaction products are eluted and the eluted radioactivity is measured in a scintillation counter as described in Example 1.

A positive signal from the tube, in which R3 had been annealed, shows that at least a part of the K-ras gene in the sample have mutated to a valine (encoded by GTT), an aspartic acid (GAT) or an alanine (GCT) residue in position 12.

A positive signal from the tube, in which R4 had been annealed, shows that there is a cysteine (TGT), a serine (AGT) or an arginine (CTG) residue in position 12 in at least a part of the K-ras genes.

Lack of signal from both tubes shows that codon 12 in both alleles is the normal GGT encoding a glycine residue.

B. Characterization of the Mutation in Codon 12

The exact characterization of the mutation is done by adding to both tubes a mixture of [$^{32}$P]-dATP, [$^{35}$S]-dGTP, [$^{3}$H]-dTTP and ddCTP to a final concentration of 1 µM in 15 µl. The [$^{32}$P]-dATP and the [$^{35}$S]-dGTP are diluted in unlabelled dATP and dGTP, respectively, to yield similar specific activities as that of the [$^{3}$H]-dTTP (about 100 Ci/mmol). The difference in scintillation counting efficiency between the three radioisotopes is taken into account to design a reaction mixture, which will give equal cpm values in the channels used for measurement (see below).

One unit of T7 DNA polymerase is added and the reaction is allowed to proceed for 5 min. at 37° C. The particles are washed and the reaction products are eluted as described in Example 1.

The radioactivity emitted by [$^{3}$H], [$^{35}$S] and [$^{32}$P] in the eluted product is measured simultaneously in a scintillation counter. In a Rackbeta 1219 counter (Pharmacia/Wallac) the following window settings are used: for measurement of [$^{3}$H]: channels 10–90, for measurement of [$^{35}$S] channels 95–145 and for measurement of [$^{32}$P] channels 170–220. Before interpretation of the results, corrections for the overflow of signal from the [$^{35}$S] to the [$^{3}$H] channels (24%) and from the [$^{32}$P] to the [$^{35}$S] channels (13%) are done.

The results are interpreted as specified in the table below:

| Detection step | Signal from | | | Result | |
|---|---|---|---|---|---|
| Primer | $^{3}$H | $^{35}$S | $^{32}$P | Codon 12 | Amino acid |
| R3 | + | − | − | GAT | aspartic acid |
| R3 | − | + | − | GCT | alanine |
| R3 | − | − | + | GTT | valine |
| R3 | − | − | − | GGT | glycine |
| R4 | + | − | − | AGT | serine |
| R4 | − | + | − | CGT | arginine |
| R4 | − | − | + | TGT | cysteine |
| R4 | − | − | − | GGT | glycine |

The mutations in codon 12 of the K-ras gene can optionally be determined as described above, but performing the PCR with biotinylated primer R2 and primer R1. A primer complementary to the opposite strand of the K-ras gene is then used as detection step primer:

```
R5: 5'-AAC TTG TGG TAG TTG GAG CT     (14-33)

R6: 5'-ACT TGT GGT AGT TGG AGC TG     (15-34)
```

We claim:

1. A method for detecting the presence of one or more specific nucleotides at a predetermined target position in a target nucleic acid, the method comprising the steps of:
   (a) providing an analyzable amount of the target nucleic acid in a single stranded form;
   (b) hybridizing the target nucleic acid with a detection primer to form a target-nucleic-acid/detection-primer hybrid, the detection primer comprising a detection-primer nucleotide sequence having a primer-extension-initiation 3'-end nucleotide which constitutes a 3' end of the detection primer, the detection-primer nucleotide sequence being complementary to a primer-hybridizing nucleotide sequence of the target nucleic acid with a nucleotide in the target nucleic acid complementary to the primer-extension-initiation 3'-end nucleotide of the detection-primer nucleotide sequence defining a primer-end complement nucleotide, the primer-hybridizing nucleotide sequence of the target nucleic acid extending towards the 3' end of the target nucleic acid from the primer-end complement nucleotide, the primer-end complement nucleotide being located in the target nucleic acid at a position 3'-ward of the predetermined target position, the position of the primer-end complement nucleotide being subject to a constraint that no nucleotide of the same type as the one or more specific nucleotides to be detected be located in the target nucleic acid in any position between the position of the primer-end complement nucleotide and the predetermined target position;
   (c) forming an extension-reaction mixture by exposing the target-nucleic-acid/detection-primer hybrid to an admixture of a polymerization agent and a plurality of nucleoside triphosphates, the nucleoside triphosphates of the admixture including at least one deoxynucleotide and at least one chain-terminating nucleotide analogue, at least one deoxynucleotide defining a labeled deoxynucleotide comprising a detectable label or an attachment moiety capable of binding a detectable label, each deoxynucleotide of the admixture of nucleoside triphosphates being complementary to a nucleotide which differs from any nucleotide to which a chain-terminating nucleotide analogue of the admixture is complementary, the plurality of nucleoside triphosphates of the admixture being such that, if a labeled deoxynucleotide is complementary to a specific nucleotide at the predetermined target position, a detectable primer-extension product is formed of the detection primer extended to include an extension portion incorporating the labeled deoxynucleotide; and
   (d) analyzing the extension-reaction mixture from step (c) for the presence or absence of a detectable label in association with a labeled deoxynucleotide incorporated in an extension portion of a primer extension product to detect the presence of the corresponding specific nucleotide at the target position in the target nucleic acid.

2. A method for detecting the presence of one or more specific nucleotides at a predetermined target position in a target nucleic acid, the method comprising the steps of:
   (a) providing an analyzable amount of the target nucleic acid in a single stranded form;
   (b) hybridizing the target nucleic acid with a detection primer to form a target-nucleic-acid/detection-primer hybrid, the detection primer comprising a detection-primer nucleotide sequence having a primer-extension-initiation 3'-end nucleotide which constitutes a 3' end of the detection primer, the detection-primer nucleotide sequence being complementary to a primer-hybridizing nucleotide sequence of the target nucleic acid with a nucleotide in the target nucleic acid complementary to the primer-extension-initiation 3'-end nucleotide of the detection-primer nucleotide sequence defining a primer-end complement nucleotide, the primer-hybridizing nucleotide sequence of the target nucleic acid extending towards the 3' end of the target nucleic acid from the primer-end complement nucleotide, the primer-end complement nucleotide being located in the target nucleic acid at a position 3'-ward of the predetermined target position, the position of the primer-end complement nucleotide being subject to a constraint that no nucleotide of the same type as the one or more specific nucleotides to be detected be located in the target nucleic acid in any position between the position of the primer-end complement nucleotide and the predetermined target position;
   (c) forming an extension-reaction mixture by exposing the target-nucleic-acid/detection-primer hybrid to an admixture of a polymerization agent and a plurality of nucleoside triphosphates, the nucleoside triphosphates of the admixture including at least one deoxynucleotide and at least one chain-terminating nucleotide analogue, at least one chain-terminating nucleotide analogue defining a labeled chain-terminating nucleotide analogue comprising a detectable label or an attachment moiety capable of binding a detectable label, each deoxynucleotide of the admixture of nucleoside triphosphates being complementary to a nucleotide which differs from any nucleotide to which a chain-terminating nucleotide analogue of the admixture is complementary, the plurality of nucleoside triphosphates of the admixture being such that, if a labeled chain-terminating nucleotide analogue is complementary to a specific nucleotide at the predetermined target position, a detectable primer-extension product is formed of the detection primer extended to include an extension portion terminated with the labeled chain-terminating nucleotide analogue; and
   (d) analyzing the extension-reaction mixture from step (c) for the presence or absence of a detectable label in association with a labeled chain-terminating nucleotide analogue terminating an extension portion of a primer extension product to detect the presence of the corresponding specific nucleotide at the target position in the target nucleic acid.

3. A method according to either of claims 1 or 2, wherein the target nucleic acid is obtained or derived from the cells of a patient and the detection of the specific nucleotide indicates predisposition to a genetic disease in the patient.

4. A method according to either of claims 1 or 2, wherein the analyzable amount of target nucleic acid is obtained by performing an amplification reaction on a sample of nucleic acid.

5. A method according to either of claims 1 or 2 wherein the target nucleic acid comprises an attachment moiety.

6. A method according to claim 5 wherein the target nucleic acid is immobilized on a solid matrix during step (b).

7. A method according to claim 5 wherein the target nucleic acid is immobilized on a solid matrix during step (c).

8. A method according to either of claims 1 or 2 in which the primer-end complement nucleotide is located in the target nucleic acid at a position immediately adjacent to the predetermined target position.

9. A method according to either of claims 1 or 2 wherein the detection-primer nucleotide sequence is from 10 to 40 nucleotides in length.

10. A method according to claim 1 wherein the nucleoside triphosphates of paragraph (c) include at least two deoxynucleotides, at least one of which deoxynucleotide comprises a detectable label or an attachment moiety capable of binding a detectable label.

11. A method according to either of claims 1 or 2 wherein each deoxynucleotide of the nucleoside triphosphates of paragraph (c) is a deoxyribonucleoside triphosphate selected from the group consisting of dATP, dGTP, dCTP, dUTP, and dTTP.

12. A method according to claim 1 wherein each deoxynucleotide of the nucleoside triphosphates of paragraph (c) is a deoxyribonucleoside triphosphate selected from the group consisting of dATP, dGTP, dCTP, dUTP, and dTTP and in which the detectable label is a radioisotope.

13. A method according to either of claims 1 or 2 wherein each chain-terminating nucleotide analogue of the nucleoside triphosphates of paragraph (c) is a dideoxyribonucleotide selected from the group consisting of ddATP, ddGTP, ddCTP, and ddTTP.

14. A method according to claim 2 wherein each chain-terminating nucleotide analogue of the nucleoside triphosphates of paragraph (c) is a dideoxyribonucleotide selected from the group consisting of ddATP, ddGTP, ddCTP, and ddTTP and in which the detectable label is a fluorescent group.

15. A method according to either of claims 1 or 2, wherein the polymerization agent is a DNA polymerase.

16. A method according to either of claims 1 or 2, wherein the primer extension product is removed from the target nucleic acid prior to analysis.

* * * * *